United States Patent [19]
Russ et al.

[11] Patent Number: 5,607,481
[45] Date of Patent: Mar. 4, 1997

[54] FIBER-REACTIVE ANTHRAQUINONE DYES

[75] Inventors: Werner H. Russ, Flörsheim; Christian Schumacher, Kelkheim, both of Germany

[73] Assignee: Hoechst Aktiengesellschaft, Germany

[21] Appl. No.: 600,828

[22] Filed: Feb. 13, 1996

[51] Int. Cl.⁶ .............................. D06P 5/15; D06P 1/382; D06P 1/384; C07D 251/40
[52] U.S. Cl. .................. 8/463; 8/676; 8/677; 8/678; 8/679; 8/918; 8/924; 8/549; 544/189
[58] Field of Search ........................... 544/187–189; 8/549, 676, 677, 678, 679, 463

[56] References Cited

U.S. PATENT DOCUMENTS

| 4,436,906 | 3/1984 | Niwa et al. | 544/187 |
| 5,393,884 | 2/1995 | Pedemonte et al. | 544/189 |

FOREIGN PATENT DOCUMENTS

94/29282  12/1994  WIPO .

*Primary Examiner*—Margaret Einsmann
*Attorney, Agent, or Firm*—Connolly & Hutz

[57] ABSTRACT

Fiber-reactive anthraquinone dyes Anthraquinone dyes of the formula (1)

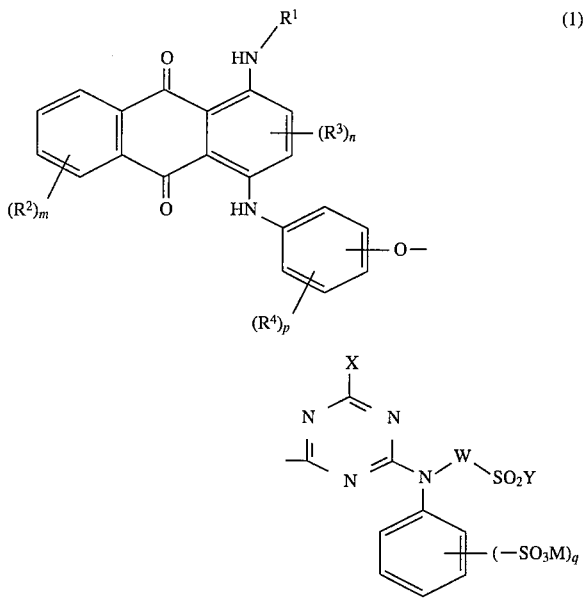

in which the variables are defined in the disclosure, exhibit excellent fastness properties, in particular chlorine fastness, light fastness and wash fastness, and give good fixation yields.

15 Claims, No Drawings

FIBER-REACTIVE ANTHRAQUINONE DYES

The present invention is in the technical field of anthraquinoid fiber-reactive dyes.

Anthraquinone dyes have been widely described in the literature. They are distinguished by their brilliance, good light fastness properties and the stability of the chromophore, not only under acidic, but also under basic conditions. However, they have the disadvantage of high raw material costs and comparatively low molar extinction. For this reason, when dyeing and printing substrates, it is important that the dyes not only have superior fastness properties and improved process characteristics, but can also be prepared at competitive costs.

Almost all important anthraquinoid reactive dyes are derivatives of bromamine acid (4-bromo-1-aminoanthraquinone-2-sulfonic acid), which in most cases is reacted with a fiber-reactive amine component, in which the fiber-reactive group can be linked to the amino group through aliphatic or, more frequently, aromatic bridging members (A. H. M. Renfrew, Rev. Prog. Color. Relat. Top. 15 (1985) 15).

One of the most important known reactive dyes for preparing brilliant, fast, blue reactive dyeings on textiles is C.I. Reactive Blue 19 of the formula (A), which was mentioned for the first time in DE-A-965,902. The course of the synthesis has been described in numerous publications.

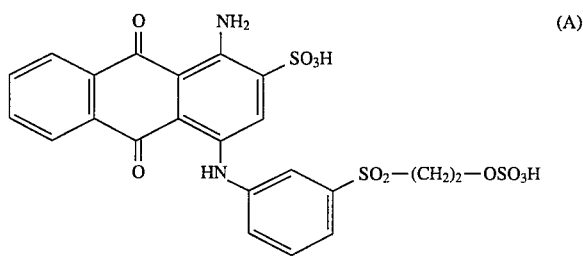
(A)

In most cases, the known anthraquinone dyes have the disadvantage that their synthesis is complicated, resulting in unsatisfactory product and space-time yields. Other brilliant blue dyes, for example azo dyes, often require metal complexation for achieving good fastness properties, a procedure which increasingly gives rise to environmental concern.

PCT/US 94/06727 describes anthraquinone dyes containing a fiber-reactive triazine radical linked through a p-aminophenol unit. However, these dyes are disadvantageous with respect to their color strength and preparability.

The object of the present invention was to provide new brilliant blue anthraquinone dyes having excellent fastness properties, in particular chlorine fastness, light fastness and wash fastness, and good fixation yields, which overcome the abovementioned disadvantages of the prior art.

It has been found that the compounds of the formula (1) defined below surprisingly meet the necessary requirements.

The present invention relates to anthraquinone compounds of the formula (1),

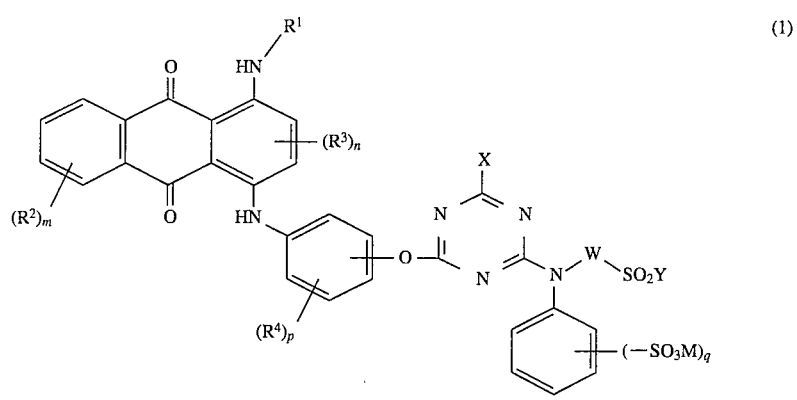

in which $R^1$ is hydrogen, $C_1$–$C_6$-alkylcarbonyl, $C_6$-arylcarbonyl, $C_1$–$C_6$-alkyl, $C_3$–$C_6$-cycloalkyl or phenyl where $C_1$–$C_6$-alkyl, $C_6$-arylcarbonyl $C_3$–$C_6$-cycloalkyl and phenyl can be substituted by one or more radicals selected from the group consisting of hydroxyl, sulfo, carboxyl, $C_1$–$C_4$-alkyl, $C_1$–$C_4$-alkoxy, halogen, cyano, amino and nitro, $R^2$ is sulfo or carboxyl, m is 0 to 2, $R^3$ is sulfo, carboxyl or halogen, such as chlorine or bromine, n is 0 or 1, $R^4$ is sulfo, carboxyl, $C_1$–$C_4$-alkyl or $C_1$–$C_4$-alkoxy, p is 0 to 2, W is a $C_1$–$C_6$-alkylene group, Y is vinyl or —$CH_2CH_2$-L in which L is a group which can be eliminated under alkaline conditions, M is hydrogen or an alkali metal or a stoichiometric equivalent of an alkaline earth metal, q is 0 or 1, and is halogen, hydroxyl, $C_1$–$C_4$-alkyloxy, $C_6$-aryloxy, cyanamino, amino, carboxy-($C_1$–$C_4$)-alkylamino, $C_1$–$C_4$-alkylamino, di-($C_1$–$C_4$-alkyl) amino or $C_6$-arylamino where the alkyl and aryl radicals of the alkylamino and arylamino groups mentioned are unsubstituted or contain 1 to 5 substituents selected from the group consisting of hydroxyl, $C_1$–$C_4$-alkoxy, carboxyl, sulfo, sulfato, $C_1$–$C_4$-alkylsulfonyl, $C_6$-arylsulfonyl, halogen, cyano and nitro, or is the radical of a heterocyclic or aliphatic amine which may contain 1 to 2 further hetero atoms selected from the group consisting of N, O and S and can be substituted by a carboxyl radical or an aminocarbonyl radical, or is the group —$NR^9R^{10}R^{11}$ in which $R^9$, $R^{10}$ and $R^{11}$, independently of one another, are hydrogen or $C_1$–$C_4$-alkyl.

For the purposes of the present invention, preference is given to compounds of the formula (1) in which R¹ is hydrogen, $C_1$–$C_4$-alkyl, $C_5$–$C_6$-cycloalkyl, acetyl, benzoyl, phenyl or methylphenylcarbonyl or $C_1$–$C_4$alkyl, $C_5$–$C_6$-cycloalkyl or phenyl each of which is substituted by 1 to 3 radicals selected from the group consisting of hydroxyl, sulfo, carboxyl, methyl, ethyl, methoxy, ethoxy, fluorine, chlorine, bromine, cyano or nitro.

Particular preference is given to those compounds of the formula (1) in which

R¹ is hydrogen.

Furthermore, preference is given to compounds of the formula (1) in which

R³ is a sulfo group which is in the ortho position relative to the NH-R¹ group.

Furthermore, preference is given to compounds of the formula (1) in which

R⁴ is sulfo, carboxyl, methyl, ethyl, methoxy or ethoxy.

Furthermore, preference is given to compounds of the formula (1) in which

W is $C_2$–$C_3$-alkylene, preferably 1,2-ethylene or 1,3-propylene.

Furthermore, preference is given to compounds of the formula (1) in which

L is chlorine, bromine, —$OSO_3M$, —$SSO_3M$, —$OPO_3M_2$, preferably —$OSO_3M$ or chlorine, where M is hydrogen or an alkali metal.

Furthermore, preference is given to compounds of the formula (1) in which m is 0, n is 1, p is 0 or 1, and q is 0.

Furthermore, preference is given to compounds of the formula (1) in which

X is fluorine, chlorine, cyanamino, amino, carboxymethylamino, β-carboxyethylamino, β-sulfoethylamino, N-methyl-β-sulfoethylamino, β-sulfatoethylamino, β-hydroxyethylamino, bis(β-hydroxyethyl)amino, pyrrolidino, piperidino, piperazino, morpholino, pyridin-1-yl, 3-carboxypyridin-1-yl, 3-aminocarbonylpyridin-1-yl or trimethylammonium.

Furthermore, preference is given to compounds of the formula (1) in which the substituted-O-triazinyl radical is in the para position relative to the NH group of the phenyl ring.

Particularly preferred dyes are compounds of the formulae (1a), (1b), (1c), (1d) and (1e)

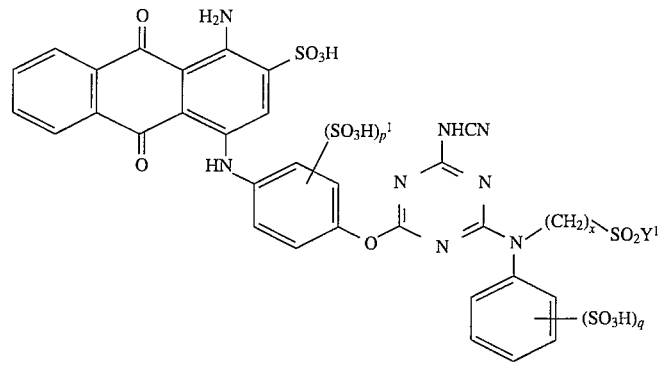

(1a)

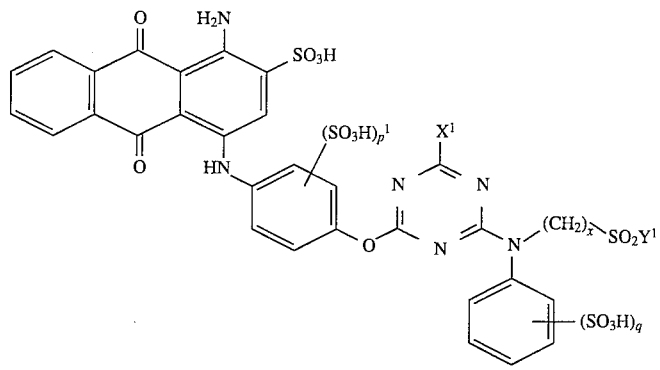

(1b)

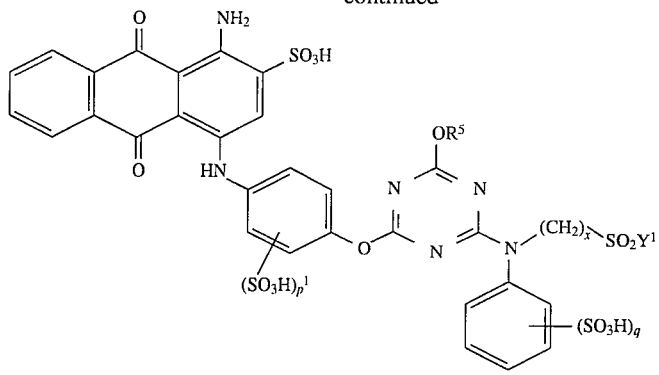

(1c)

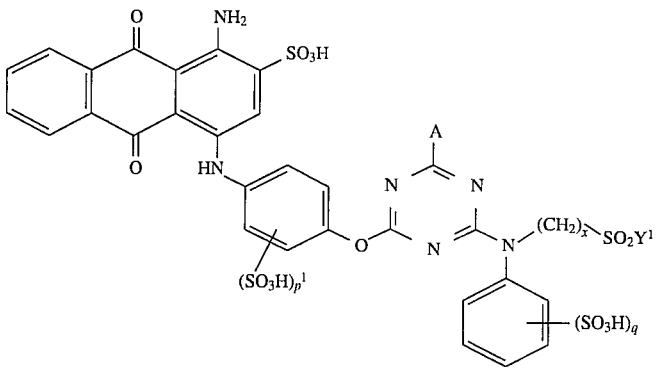

(1d)

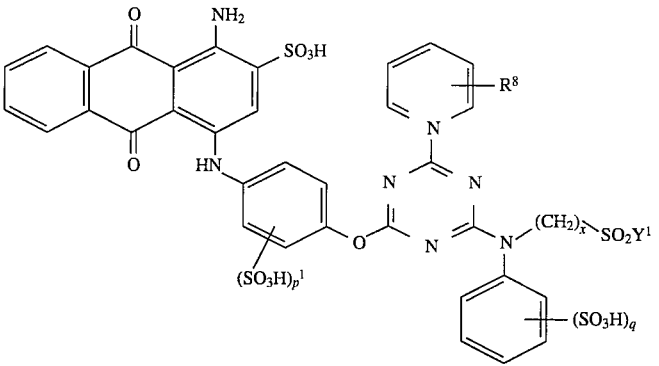

(1e)

in which x is 2 or 3, $X^1$ is chlorine or fluorine, $R^5$ is methyl, ethyl or phenyl, A is amino, carboxymethylamino, β-carboxyethylamino, β-sulfoethylamino, N-methyl-β-sulfoethylamino, β-sulfatoethylamino, β-hydroxyethylamino, bis(β-hydroxyethyl)eunino, morpholino, piperidino, pyrrolidino or trimethylammonium, $R^8$ is hydrogen, euninocarbonyl or carboxyl, $Y^1$ is β-sulfatoethyl, β-chloroethyl or vinyl and $R^1$=0 or 1.

Particular preference is given to dyes of the formula (1f)

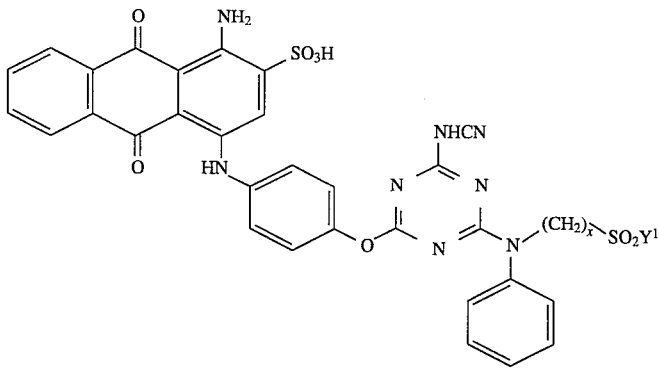

(1f)

in which x and $Y^1$ have one of the abovementioned meanings. The preferred dyes of the formulae (1a), (1c), (1d), (1e) and (1f) have the advantage that they do not contain any organically bound halogen if $Y^1$ is β-sulfatoethyl or vinyl, i.e. they are ecologically particularly advantageous.

Furthermore, the present invention provides a process for preparing the anthraquinone dyes according to the invention (1), which process comprises reacting a compound of the formula (2)

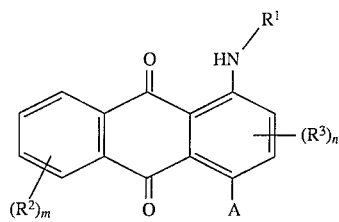

in which A is fluorine, chlorine, bromine, iodine, sulfo or nitro, in particular bromine, and the radicals $R^1$, $R^2$ and $R^3$ have one of the abovementioned meanings with a compound of the formula (3)

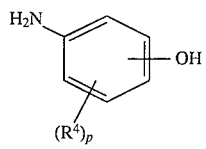

in which $R^4$ and p have one of the abovementioned meanings, in the presence of a copper(I) or a copper(II) compound or a mixture thereof, to give a compound of the formula (4)

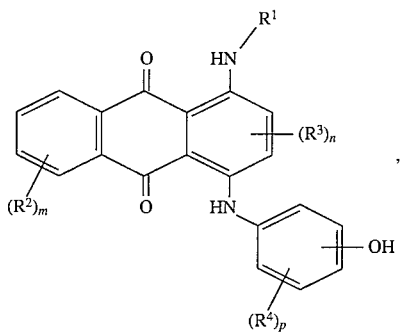

reacting the compound of the formula (4) either with a compound of the formula (5)

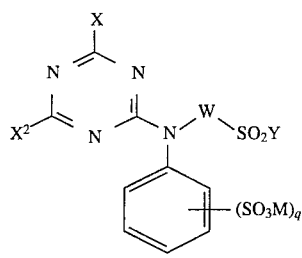

in which X, W, Y, M and q have one of the abovementioned meanings and $X^2$ is halogen, to give the compound of the formula (1), or reacting the compound of the formula (4) first with a compound of the formula (6)

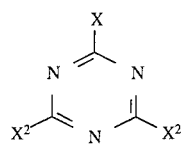

in which X and $X^2$ have the abovementioned meanings, to give a compound of the formula (7)

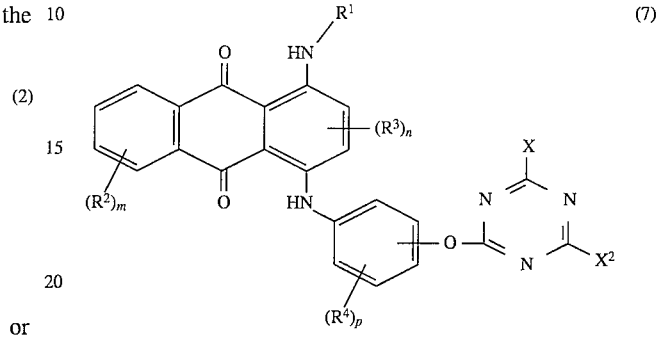

and reacting the compound of the formula (7) with an amine of the formula (8)

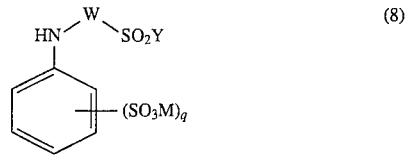

in which W, Y, M and q have one of the abovementioned meanings, to give the compound of the formula (1).

The preferred process variant for preparing the anthraquinone compounds of the formula (1) is the route described above via the compounds of the formulae (6), (7) and (8).

It is known from the literature that Ullmann condensations of bromamine acid with aromatic amines are best carried out in the presence of copper(I) compounds (J.Chem. Soc. Perkin II, 1974, 676 and Coll. Czech. Chem. Commun. 46 (1981), 92). Preferably, a catalytic amount, for example 0.5 to 5% by weight, preferably 0.8 to 2% by weight, relative to the compound of the formula (2), of a copper(I) compound, preferably of a copper(I) halide or a copper(I) pseudohalide, such as CuCl, CuBr, CuI or CuCN, is used and the condensation is carried out at temperatures of 30° to 90° C., preferably 50° to 70° C., and pH values of 5 to 10, preferably 6 to 9.

It has now been found that the condensation of the compounds of the formulae (2) and (3) can surprisingly also be carried out in the presence of copper (II) compounds, such as copper (II) sulfate, copper (II) nitrate, copper (II) chloride, copper (II) bromide, copper (II) carbonate or copper (II) hydroxide.

Accordingly, the present invention also provides a process for preparing a compound of the formula (4) by condensing a compound of the formula (2) with a compound of the formula (3) in the presence of a copper(II) compound. Also in the case where a copper(II) compound is used, it preferred to choose the amounts, temperatures and pH values mentioned for the case of using a copper(I) compound.

Not only when copper(I) compounds but also when copper(II) compounds are used, the condensation is carried out in an aqueous or aqueous organic medium in suspension or solution. If the reaction is carried out in an aqueous organic medium, the organic medium is, for example, acetone, dimethylformamide, dimethyl sulfoxide or N-methylpyrrolidone. Advantageously the hydrohalic acid released during condensation is continuously neutralized by adding aqueous alkali metal hydroxides, alkali metal carbonates, alkali metal phosphates, alkali metal silicates or alkali metal bicarbonates. The relative molar amounts of the compounds of the formulae (2) and (3) are advantageously 1:1 to 1:1.4.

The reaction of the compound of the formula (4) with the compound of the formula (5) is advantageously carried out at temperatures of 50° to 100° C. and pH values of 3 to 7, if $X^2$ is chlorine or bromine, and advantageously at temperatures of −5° to 50° C., preferably 0° to 25° C., and pH values of 4 to 10, if $X^2$ is fluorine. The relative molar amounts of the compounds of the formulae (4) and (5) are advantageously 1:1 to 1:1.5.

The reaction of the compound of the formula (4) with the compound of the formula (6) is advantageously carried out at temperatures of 0° to 50° C., preferably 20° to 40° C., and pH values of 4 to 10, preferably 7 to 9, if $X^2$ is chlorine or bromine, and advantageously at temperatures of −5° to 25° C., preferably −2° to +5° C., and pH values of 3 to 5, if $X^2$ is fluorine. The relative molar amounts of the compounds of the formulae (4) and (6) are advantageously 1:1 to 1:1.5.

The reaction of the compound of the formula (7) with the amine of the formula (8) can be carried out under surprisingly mild conditions, at temperatures of 30° to 90° C., preferably 40° to 70° C., and pH values of 4 to 7, preferably 5 to 6. The relative molar amounts of the compounds of the formulae (7) and (8) are advantageously 1:1 to 1:1.5.

The anthraquinone dyes of the formula (I) according to the invention are precipitated, for example, by pouring them onto ice/water with stirring. Neutralization with alkali metal hydroxide, alkali metal phosphate, alkali metal silicate, alkali metal carbonate or alkali metal bicarbonate gives the aqueous solutions of the alkali metal salts of the compounds of the formula (1). The dyes can be isolated from this solution, for example, by salting out or by spray drying. It is particularly advantageous to use the standardized aqueous formulations, to which, if desired, buffer substances are added and which, if desired, can be concentrated, directly for the corresponding technical applications.

Anthraquinone dyes of the formula (1) in which X is the radical of one the amines defined above ($X=X^{10}$) can also be prepared by first preparing the corresponding anthraquinone dye of the formula (1) in which X is chlorine or fluorine ($X=X^2$) by one of the methods mentioned and then reacting this dye with the corresponding amine at temperatures of 40° to 100° C. and pH values of 3 to 8 in relative molar amounts of, advantageously, 1:1 to 1:2.

Examples of such amines mentioned include the following: ammonia, methylamine, ethylamine, ethanolamine, diethanolamine, β-sulfoethylamine, N-methyl-β-sulfoethylamine, β-carboxyethylamine, carboxymethylamine, 3-carboxypyridine, 3-aminocarbonylpyridine, pyridine, morpholine, pyrrolidine, piperidine, piperazine, N'-hydroxyethylpiperazine, N'-sulfatoethylpiperazine, aniline, 3-sulfoaniline, 4-sulfoaniline, 4-carboxyaniline, 4-methylaniline, 4-methoxyaniline, 4-methoxy-3-sulfoaniline and 4-methyl-3-sulfoaniline.

Accordingly, the invention also provides a process for preparing an anthraquinone compound of the formula (1A)

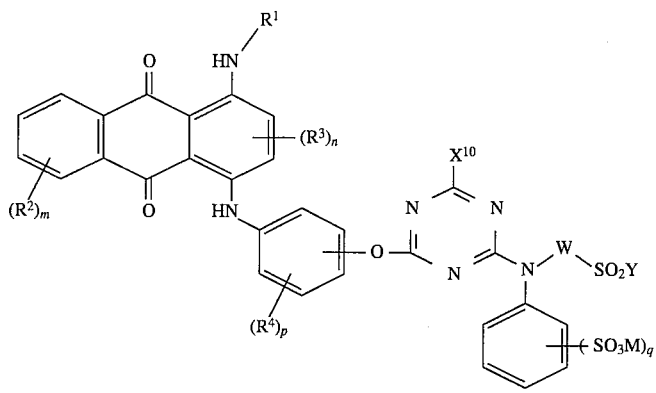

in which $R^1$, $R^2$, $R^3$, $R^4$, W, Y, M, m, n, p and q have one of the meanings defined in claim 1 and $X^{10}$ is amino, cyanamino, carboxy-($C_1$–$C_4$)-alkylamino, $C_1$–$C_4$-alkylamino, di-($C_1$–$C_4$-alkyl)amino, $C_6$-arylamino where the alkyl and aryl radicals of the alkylamino and arylamino groups mentioned are unsubstituted or contain 1 to 5 substituents selected from the group consisting of hydroxyl, $C_1$–$C_4$-alkoxy, carboxyl, sulfo, sulfato, $C_1$–$C_4$-alkylsulfonyl, $C_6$-arylsulfonyl, halogen, cyano and nitro, or is the radical of a heterocyclic or aliphatic amine, which may contain 1 to 2 further hetero atoms selected from the group consisting of N, O and S and can be substituted by a carboxyl radical or an aminocarbonyl radical, or is the group $-NR^9R^{10}R^{11}$ in which $R^9$, $R^{10}$ and $R^{11}$, independently of one another, are hydrogen or $C_1$–$C_4$-alkyl, which process comprises reacting an anthraquinone compound of the formula (1B)

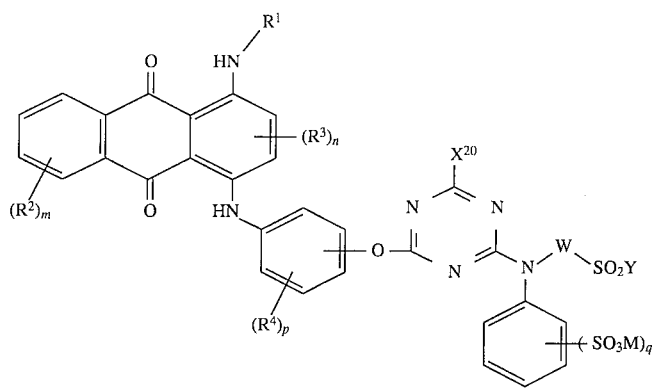

(1B)

in which $X^{20}$ is chlorine or fluorine, with ammonia, $H_2NCN$, a carboxy-$(C_1-C_4)$alkylamine, $C_1-C_4$-alkylamine, di-$(C_1-C_4$-alkyl)amine, $C_6$-arylamine where the alkyl and aryl radicals of the alkylamino and arylamino groups mentioned are unsubstituted or contain 1 to 5 substituents selected from the group consisting of hydroxyl, $C_1-C_4$-alkoxy, carboxyl, sulfo, sulfato, $C_1-C_4$-alkylsulfonyl, $C_6$-arylsulfonyl, halogen, cyano and nitro, or with a heterocyclic or aliphatic amine, which may contain 1 to 2 further hetero atoms selected from the group consisting of N, O and S and can be substituted by a carboxyl radical or an aminocarbonyl radical, or with a mono-, di- or tri-$(C_1-C_4$-alkyl)ammonium salt.

Examples of compounds of the formula (2) include the following:
1-amino-4-bromo-, 1-amino-4-bromo-2-sulfo-, 1-amino-2, 4-dibromo-, 1-methylamino-2-carboxy-4-bromo-, 1-ethylamino-2-carboxy-4-bromo-, 1-isopropylamino-2-carboxy-4-bromo-, 1-amino-4-bromo-2,6-disulfo-, 1-amino-4-bromo-2,7-disulfo-, 1-amino-4-bromo-2,5,8-trisulfo-, 1-propylamino-4-bromo-2-sulfo-, 1-amino-4-bromo-2-carboxy-, 1-amino-4-bromo-2-sulfo-6-carboxy-, 1-amino-4-bromo-2-sulfo-7-carboxy-, 1-methylamino-4-bromo-, 1-methylamino-4-bromo-2-sulfo-, 1-ethylamino-4-bromo-2-sulfo-, 1-(β-hydroxyethyl)amino-4-bromo-2-sulfo-, 1-phenylamino-4-bromo-2-sulfo-, 1-amino-2-bromo-4-nitro-, 1-cyclohexylamino-4-bromo-, 1-benzoylamino-4-bromo-, 1-acetylamino-4-bromo-, 1-cyclohexylamino-4-bromo-5-sulfo-, 1-cyclohexylamino-4-bromo-6-sulfo-, 1-cyclohexylamino-4-bromo-7-sulfo- or 1-cyclohexylamino-4-bromo-8-sulfoanthraquinone.

A particularly preferred anthraquinone component is 1-amino-4-bromo-2-sulfoanthraquinone. The preparation of the anthraquinone compounds mentioned is known to one skilled in the art and described, for example, in Houben-Weyl, Vol. 7/3c, 4th. Edition, p. 46ff.

Examples of compounds of the formula (3) are 4-aminophenol, 4-amino-2-sulfophenol, 4-amino-3-sulfophenol, 3-aminophenol, 3-amino-4-sulfophenol, 3-amino-5-sulfophenol, 2-carboxy-4-aminophenol and 3-carboxy-4-aminophenol. The preparation of such aminophenols is known to one skilled in the art and described, for example, in Houben-Weyl, Vol. XI/1.

Compounds of the formula ( 5 ) can be prepared, for example, by reacting compounds of the formula (6) with compounds of the formula (8) (EP-A1-0,629,667).

Examples of compounds of the formula (6) are 2,4,6-trichloro-1,3,5-triazine, 2,4,6-trifluoro-1,3,5-triazine, 2-cyanamino-4,6-dichloro-1,3,5-triazine, 2-methoxy-4,6-dichloro-1,3,5-triazine, 2-ethoxy-4,6-dichloro-1,3,5-triazine, 2-phenoxy-4,6-dichloro-1,3,5-triazine and 2-amino-4,6-dichloro-1,3,5-triazine. The preparation of such triazines is known to one skilled in the art and described, for example, in DE-A-2,756,438 and DE-A-3, 930,704.

Examples of compounds of the formula (8) are 3-(N-phenyl)aminopropyl 2'-sulfatoethyl sulfone, 3-N-[3"-sulfophenyl]aminopropyl 2'-sulfatoethyl sulfone, 3-N-[4"-sulfophenyl]aminopropyl 2'-sulfatoethyl sulfone, 3 -N-[2"-sulfophenyl)aminopropyl 2'-sulfatoethyl sulfone, 2-(N-phenyl)aminoethyl 2'-sulfatoethyl sulfone, 2-N-[2"-sulfophenyl]aminoethyl 2'-sulfatoethyl sulfone, 2-N-[3"-sulfophenyl]aminoethyl 2'-sulfatoethyl sulfone and 2-N-[4"-sulfophenyl]aminoethyl 2'-sulfatoethyl sulfone. The preparation of such compounds is described, for example, in EP-A1-0,629,667 and EP-A1-0,568,876.

The compounds of the formula (1) exhibit fiber-reactive properties and possess very good dye properties. They can be used for dyeing and printing hydroxyl-, mercapto-, amino- and/or carboxamido-containing materials, in particular fiber materials. They give brilliant blue shades having excellent fastness properties, such as light fastness, wash fastness and chlorinated water fastness without requiring metal complexations. Accordingly, the dyes according to the invention are ecologically advantageous.

Accordingly, the present invention also relates to the use of the compounds of the formula (1) for dyeing and printing the materials mentioned. This is done by applying the compound of the formula (1) to the material or incorporating it in the material and fixing it on or in the material by means of heat or by using an alkaline agent.

Examples of suitable materials are native or regenerated cellulose materials, such as cotton, linen, staple viscose, filament viscose, chemically modified cellulose fibers, for example cellulose fibers modified by amino compounds, proteinaceous fibers, such as wool or silk, and synthetic polyamides, such as nylon or perlon, all of which are well known to one skilled in the art.

Examples of suitable application methods are the exhaust method in winch-dyeing machines and jet-dyeing machines or continuous dyeing methods. The dyes according to the invention are particularly suitable for dyeing and printing cellulose materials using a short-liquor application method, for example at a liquor ratio of 0,4:1 to 5:1, and for textile printing or pad-dyeing methods, such as, for example, continuous methods.

The preferred dyes (1a), (1c), (1d), (1e) and especially (1f) are particularly suitable for textile printing methods. Another characteristic feature of the preferred dyes (1a), (1c), (1d), (1e) and especially (1f) is that they can advantageously be applied in the discharge printing method.

In this description, the dyes of the present invention have been written in the form of their free acids. However, they can also be used as salts of these acids. Preferably, they are used in the form of their salts, and particularly preferably in the form of their alkali metal salts and alkaline earth metal salts, such as, for example, their sodium salts, potassium salts or lithium salts.

In the examples, percentages and parts are by weight. The absorption maxima given (lambda max) in the visible region were determined using their alkali metal salts in aqueous solution.

Example A 38.2 parts of 1-amino-4-bromo-2-sulfoanthraquinone (bromamine acid) are condensed in an aqueous suspension with 12.7 parts of 4-aminophenol with the addition of 1 part of copper(II) sulfate at a pH of 8.5 and a temperature of 70° C. over a period of 1 to 2 hours. This results in a dark blue solution. After cooling to 20°–25° C., the reaction mixture is acidified until reaching a pH of about 1, stirred at 60° C. for about 1 h, salted out with sodium chloride, and the dye chromophore 4-(4'-hydroxyphenyl)amino-1-amino-2-sulfoanthraquinone is isolated by suction filtration.

The anthraquinone compound thus obtained has the formula

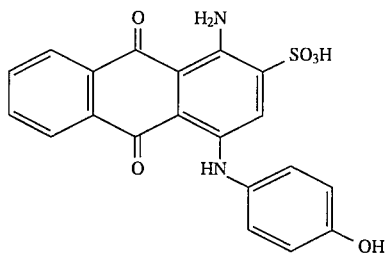

Example 1

41 parts of the anthraquinone compound from Example A are dissolved in 200 parts of water at a pH of 8.5 and a temperature of 35° C., followed by addition of 20 parts of 2-cyanamino-4,6-dichloro-1,3,5-triazine and condensation at a pH of 8 to 9 and a temperature of 35° C. The mixture is stirred for some time until reaction is complete, and 36 parts of 3-(N-phenyl)aminopropyl 2'-sulfatoethyl sulfone are then added. The reaction is carried out at a temperature of 50° C. and a pH of 8.5 over a period of about 3 h. The product is then salted out with potassium chloride or, preferably, isolated by evaporation in vacuo to give 85 parts of the dye of the formula in an HPLC purity of 90%.

The dye dyes and prints cellulose fibers in brilliant blue shades which exhibit high color strengths in combination with good levelness and very good fastness properties, in particular light fastness properties.

Example 2

41 parts of the anthraquinone compound from Example A are dissolved in 200 parts of water at a pH of 8.5 and a temperature of 40° C., followed by addition of 20 parts of 2-cyanamino-4,6-dichloro-1,3,5-triazine and condensation at a pH of 8 to 9 and a temperature of 40° C. The mixture is stirred for some time until reaction is complete, and 33 parts of 2-(N-phenyl)aminoethyl 2'-sulfatoethyl sulfone are then added. The reaction is carried out at a temperature of 50° C. and a pH of 8.5 over a period of about 3 h. The product is then salted out with potassium chloride or, preferably, isolated by evaporation in vacuo to give 82 parts of the dye of the formula

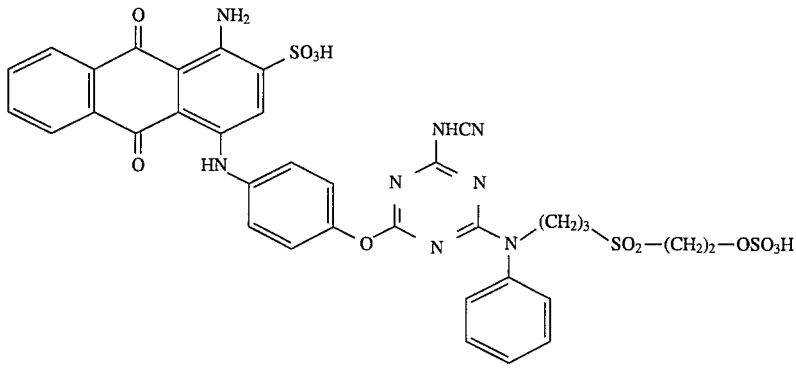

(blue (598 nm))

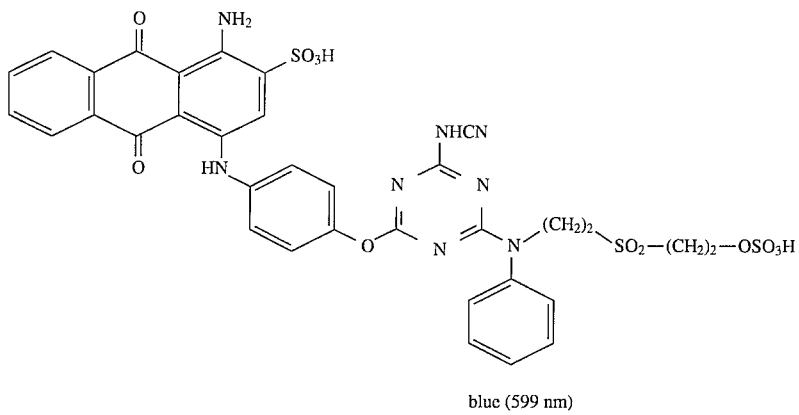

blue (599 nm)

in an HPLC purity of 84%.

The dye dyes and prints cellulose fibers in brilliant blue shades which exhibit high color strengths in combination with good levelness and very good fastness properties, in particular light fastness properties.

Example 3

41 parts of the anthraquinone compound from Example A are dissolved in 200 parts of water at a pH of 8.5 and a temperature of 40° C., followed by addition of 20 parts of 2,4,6-trichloro-1,3,5-triazine and condensation at a pH of 7 to 8 and a temperature of 0° to 5° C. The mixture is stirred for some time until reaction is complete, and 33 parts of N-phenyl-2-[(2'-sulfatoethyl)sulfonyl]-ethylamine are then added. The reaction is carried out at a temperature of 50° C. and a pH of 8.5 over a period of about 3 h. The product is then salted out with potassium chloride or, preferably, isolated by evaporation in vacuo to give 82 parts of the dye of the formula The dye dyes and prints cellulose fibers in brilliant blue shades which exhibit high color strengths in combination with good levelness and very good fastness properties, in particular light fastness properties.

Example 4

87 parts of the compound from Example 3 are dissolved in 300 parts of water at a pH of 6.5 and a temperature of 30° C., followed by addition of 8.5 parts of morpholine and condensation at a pH of 7 to 8 and a temperature of 60° C. The mixture is stirred for some time until reaction is complete. The product is then salted out with potassium chloride or, preferably, isolated by evaporation in vacuo to give 85 parts of the dye of the formula

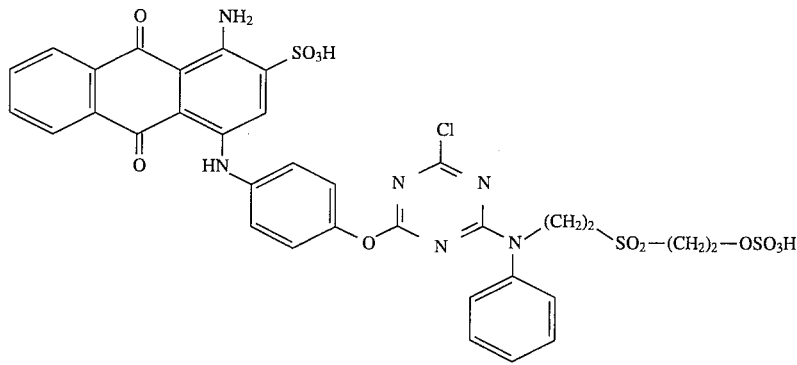

blue (600 nm)

in an HPLC purity of 87%.

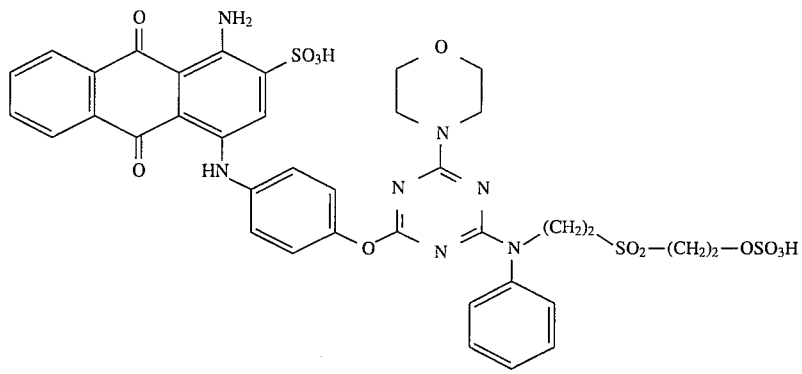

in an HPLC purity of 73%.

The dye dyes and prints cellulose fibers in brilliant blue shades which exhibit high color strengths in combination with good levelness and very good fastness properties, in particular light fastness properties.

Example 5

41 parts of the anthraquinone compound from Example A are dissolved in 500 parts of water at a pH of 8 and a temperature of 30° C. and cooled to 0° to 5° C., followed by addition of 45 parts of the compound 2-[N-phenyl-(2'-sulfatoethylsulfonyl)ethylamino]-4,6-difluoro-1,3,5-triazine disclosed in EP-A-0,568,876 and condensation at a pH of 7 to 8 and a temperature of 10° to 20° C. The mixture is stirred for some time until reaction is complete. The product is then salted out with potassium chloride or, preferably, isolated by evaporation in vacuo to give 80 parts of the dye of the formula

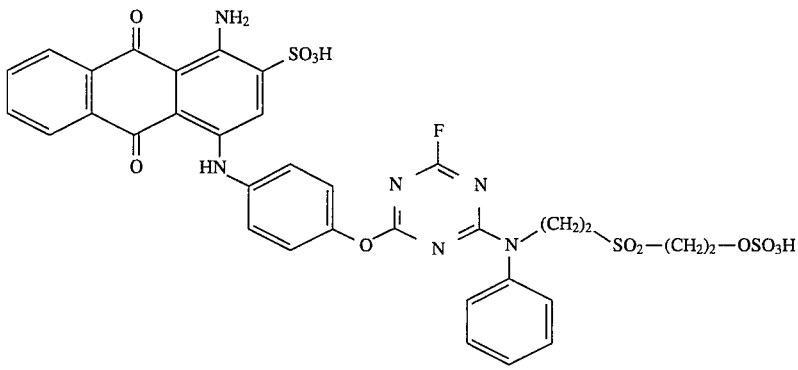

in an HPLC purity of 88%.

The dye dyes and prints cellulose fibers in brilliant blue shades which exhibit high color strengths in combination with good levelness and very good fastness properties, in particular light fastness properties.

Example 6

80 parts of the compound from Example 5 are dissolved in 300 parts of water at a pH of 6.5 and a temperature of 30° C., followed by addition of 12 parts of nicotinic acid and condensation at a pH of 3 to 4 and a temperature of 70° to 80° C. The mixture is stirred for some time until reaction is complete. The product is then salted out with potassium chloride or, preferably, isolated by evaporation in vacuo to give 90 parts of the dye of the formula

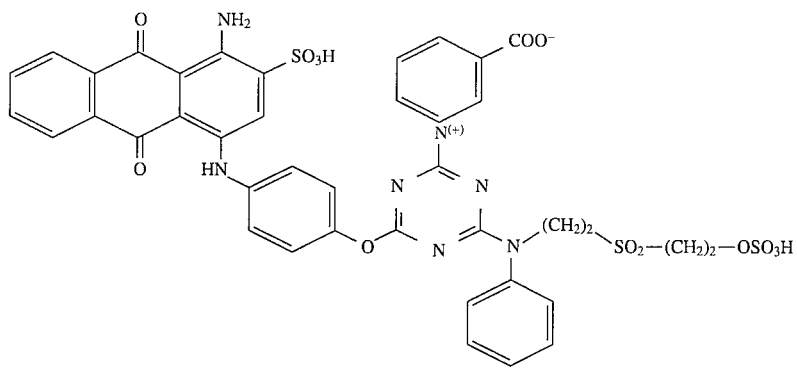

in an HPLC purity of 73%.

The dye dyes and prints cellulose fibers in brilliant blue shades which exhibit high color strengths in combination with good levelness and very good fastness properties, in particular light fastness properties.

Further dyes of the following formula according to the invention are obtained by repeating the procedure of Example 1 and using for the synthesis the corresponding precursors shown in the table.

| Ex. No. | B(1 = amino linkage) | $X^0$ | $N(Ar)-W^1-SO_2Y$ | Shade on cotton |
|---|---|---|---|---|
| 7 | 1,4-phenylene | chlorine | N-phenyl-[3'-(β-sulfatoethyl)-sulfonyl-propyl]amino | blue (602) |
| 8 | " | cyanamino | N-(3"-sulfophenyl)-[3'-(β-sulfatoethyl)-sulfonylpropyl]-amino | blue (604) |
| 9 | " | cyanamino | N-(3"-sulfophenyl)-[2'-(β-sulfatoethyl)-sulfonylethyl]-amino | blue (605) |
| 10 | 1,3-phenylene | fluorine | N-phenyl-[3'-(β-sulfatoethyl)sulfonylpropyl]-amino | blue (605) |
| 11 | 3-sulfo-1,4-phenylene | amino | N-phenyl-[3'-(β-sulfatoethyl)sulfonylpropyl]-amino | blue (606) |
| 12 | 3-sulfo-1,4-phenylene | piperidino | N-phenyl-[3'-(β-sulfatoethyl)sulfonylpropyl]-amino | blue (603) |
| 13 | 4-sulfo-1,3-phenylene | pyrrolidino | N-phenyl-[3'-(β-sulfatoethyl)sulfonylpropyl]-amino | blue (603) |
| 14 | 1,4-phenylene | (3-amino-carbonyl)-pyridinyl | N-phenyl-[3'-(β-sulfatoethyl)- | blue (603) |

-continued

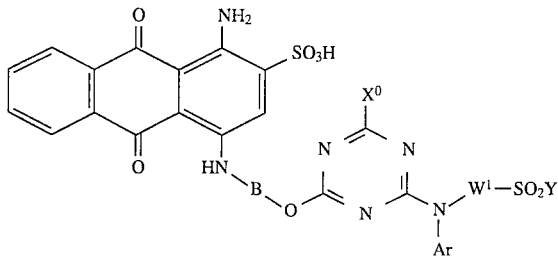

| Ex. No. | B(1 = amino linkage) | X⁰ | N(Ar)—W¹—SO₂Y | Shade on cotton |
|---|---|---|---|---|
| 15 | " | methoxy | sulfonyl-propyl]amino N-phenyl-[3'-(β-sulfatoethyl)-sulfonyl-propyl]amino | blue (603) |
| 16 | " | phenoxy | N-phenyl-[3'-(β-sulfatoethyl)-sulfonyl-propyl]amino | blue (603) |

We claim:

1. An anthraquinone compound of the formula (1),

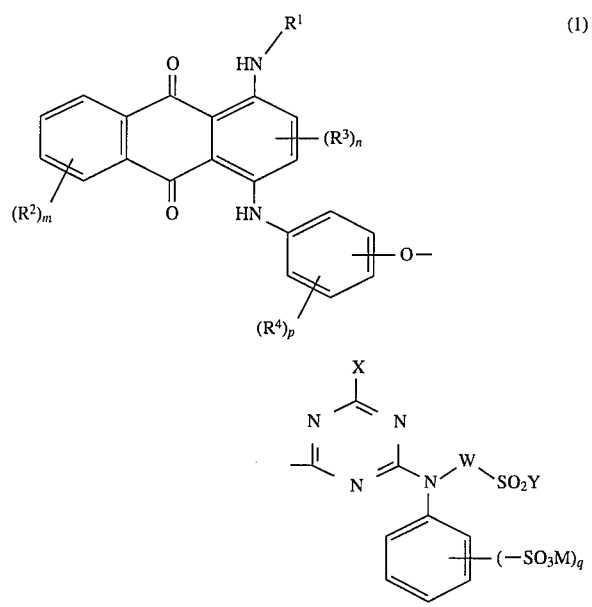

in which $R^1$ is hydrogen, $C_1$–$C_6$-alkylcarbonyl, $C_6$-arylcarbonyl, $C_1$–$C_6$-alkyl, $C_3$–$C_6$-cycloalkyl or phenyl where $C_1$–$C_6$-alkyl, $C_6$ arylcarbonyl $C_3$–$C_6$-cycloalkyl and phenyl can be substituted by one or more radicals selected from the group consisting of hydroxyl, sulfo, carboxyl, $C_1$–$C_4$-alkyl, $C_1$–$C_4$-alkoxy, halogen, cyano, amino and nitro, $R^2$ is sulfo or carboxyl, m is 0 to 2, $R^3$ is sulfo, carboxyl or halogen, n is 0 or 1, $R^4$ is sulfo, carboxyl, $C_1$–$C_4$-alkyl or $C_1$–$C_4$-alkoxy, p is 0 to 2, W is a $C_1$–$C_6$-alkylene group, Y is vinyl or —CH₂CH₂-L where L is a group which can be eliminated under alkaline conditions, M is hydrogen or an alkali metal or a stoichiometric equivalent of an alkaline earth metal, q is 0 or 1, and X is halogen, hydroxyl, $C_1$–$C_4$-alkyloxy, $C_6$-aryloxy, cyanamino, amino, carboxy-($C_1$–$C_4$)-alkylamino, $C_1$–$C_4$-alkylamino, di-($C_1$–$C_4$-alkyl)amino or $C_6$-arylamino where the alkyl and aryl radicals of the alkylamino and arylamino groups mentioned are unsubstituted or contain 1 to 5 substituents selected from the group consisting of hydroxyl, $C_1$–$C_4$-alkoxy, carboxyl, sulfo, sulfato, $C_1$–$C_4$-alkylsulfonyl, $C_6$-arylsulfonyl, halogen, cyano and nitro; or is the radical of a heterocyclic or aliphatic amine which may contain 1 or 2 further hetero atoms selected from the group consisting of N, O and S and can be substituted by a carboxyl radical or an aminocarbonyl radical; or is the group —NR⁹R¹⁰R¹¹ in which $R^9$, $R^{10}$ and $R^{11}$, independently of one another, are hydrogen or $C_1$–$C_4$-alkyl.

2. An anthraquinone compound as claimed in claim 1, wherein $R^1$ is hydrogen, $C_1$–$C_4$-alkyl, $C_5$–$C_6$-cycloalkyl, acetyl, benzoyl, phenyl or methylphenylcarbonyl or $C_1$–$C_4$-alkyl, $C_5$–$C_6$-cycloalkyl or phenyl each of which is substituted by 1 to 3 radicals selected from the group consisting of hydroxyl, sulfo, carboxyl, methyl, ethyl, methoxy, ethoxy, fluorine, chlorine, bromine, cyano and nitro.

3. An anthraquinone compound as claimed in claim 1, wherein $R^3$ is chlorine, bromine or a sulfo group which is in the ortho position relative to the NH-$R^1$ group.

4. An anthraquinone compound as claimed in claim 1, wherein W is $C_2$–$C_3$-alkylene.

5. An anthraquinone compound as claimed in claim 1, wherein W is 1,2-ethylene or 1,3-propylene.

6. An anthraquinone compound as claimed in claim 1, wherein L is chlorine, bromine, —OSO₃M, —SSO₃M or —OPO₃M₂ where M is hydrogen or an alkali metal.

7. An anthraquinone compound as claimed in claim 1, wherein m is 0, n is 1,
p is 0 or 1, and
q is 0.

8. An anthraquinone compound as claimed in claim 1, wherein

X is fluorine, chlorine, cyanamino, amine, carboxymethylamino, β-carboxyethylamino, β-sulfoethylamino, N-methyl-β-sulfoethylamino, β-sulfatoethylamino, β-hydroxyethylamino, bis(β-hydroxyethyl)amino, pyrrolidino, piperidino, piperazino, morpholino, pyridin-1-yl, 3-carboxypyridin-1-yl, 3-aminocarbonylpyridin-1-yl or trimethylammonium.

9. An anthraquinone compound as claimed in claim 1, wherein the anthraquinone compound has the formula (1a), (1b), (1c), (1d), (1e) or (1f)

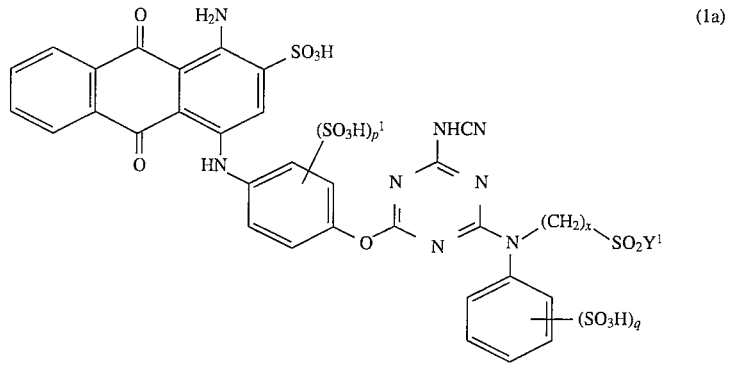

(1a)

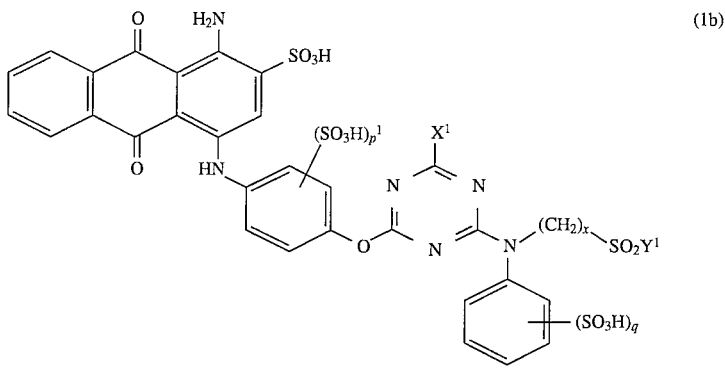

(1b)

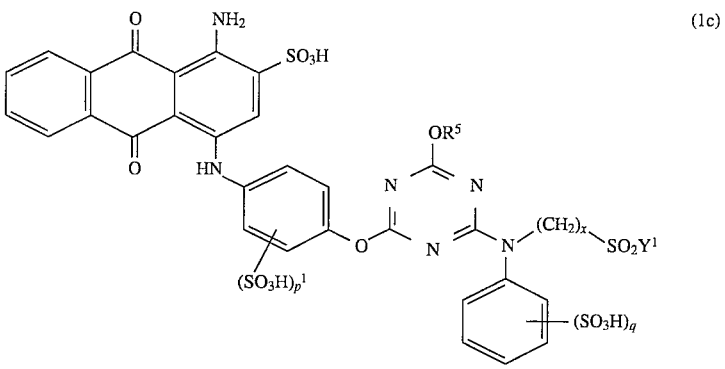

(1c)

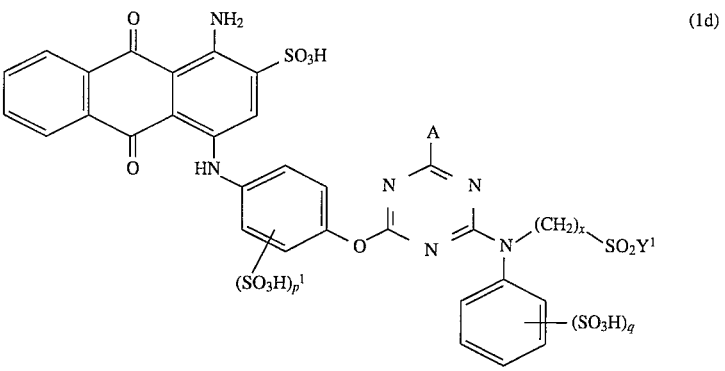

(1d)

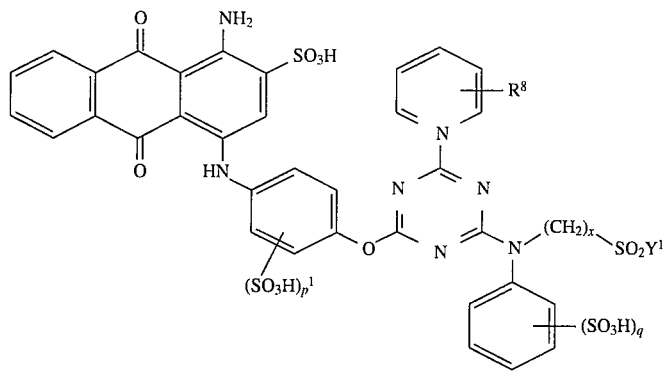

(1e)

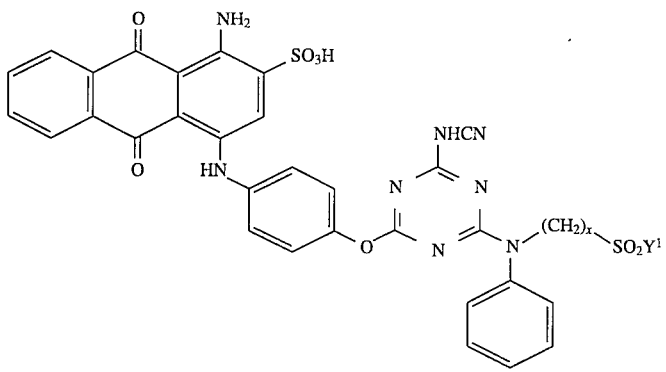

(1f)

in which x is 2 or 3, $X^1$ is chlorine or fluorine, $R^5$ is methyl, ethyl or phenyl, A is amino, carboxymethylamino, β-carboxyethylamino, β-sulfoethylamino, N-methyl-β-sulfoethylamino, β-sulfatoethylamino, β-hydroxyethylamino, bis(β-hydroxyethyl)amino, morpholino, piperidino, pyrrolidino or trimethylammonium, $R^8$ is hydrogen, aminocarbonyl or carboxyl, $Y^1$ is β-sulfatoethyl, β-chloroethyl or vinyl and $p^1$ is 0 or one.

10. A process for preparing a compound as claimed in claim 1, which process comprises reacting a compound of the formula (2)

(2)

in which A is fluorine, chlorine, bromine, iodine, sulfo or nitro, with a compound of the formula (3)

(3)

in the presence of a copper(I) or a copper(II) compound or a mixture thereof, to give a compound of the formula (4)

(4)

and reacting the compound of the formula (4) either with a compound of the formula (5)

(5)

in which $X^2$ is halogen, to give the compound of the formula (1), or reacting the compound of the formula (4) first with a compound of the formula (6)

(6)

to give a compound of the formula (7)

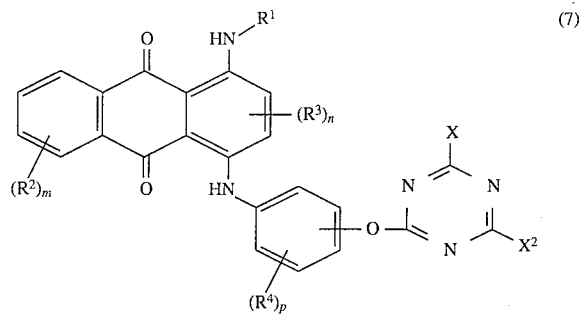

and reacting the compound of the formula (7) with an amine of the formula (8)

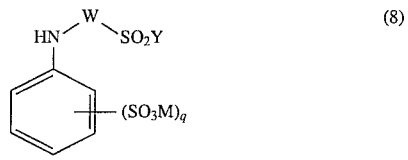

to give the compound of the formula (1).

11. The process as claimed in claim 10, wherein the copper(II) compound is copper(II) sulfate, copper(II) nitrate, copper(II) chloride, copper(II) bromide, copper(II) carbonate or copper(II) hydroxide.

12. A process for preparing an anthraquinone compound (1) as in claim 1 of the formula (1A)

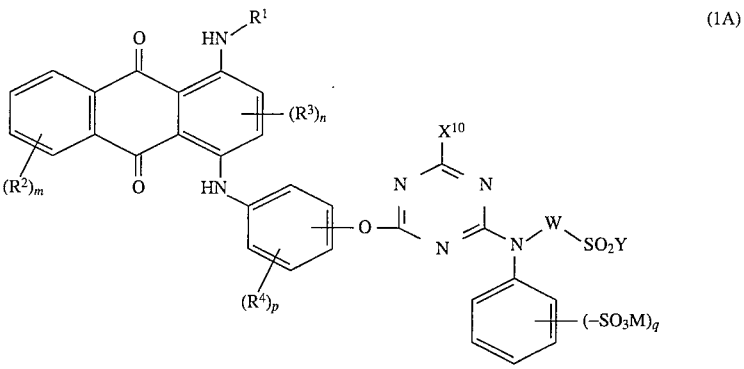

in which $R^1$, $R^2$, $R^3$, $R^4$, W, Y, M, m, n, p and q have one of the meanings defined in claim 1 and $X^{10}$ is amino, cyanamino, carboxy-$(C_1-C_4)$-alkylamino, $C_1-C_4$-alkylamino, di-$(C_1-C_4$-alkyl) amino, $C_6$-arylamino where the alkyl and aryl radicals of the alkylamino and arylamino groups mentioned are unsubstituted or contain 1 to 5 substituents selected from the group consisting of hydroxyl, $C_1-C_4$-alkoxy, carboxyl, sulfo, sulfato, $C_1-C_4$-alkylsulfonyl, $C_6$-arylsulfonyl, halogen, cyano and nitro, or is the radical of a heterocyclic or aliphatic amine, which may contain 1 to 2 further hetero atoms selected from the group consisting of N, O and S and can be substituted by a carboxyl radical or an aminocarbonyl radical, or is the group —$NR^9R^{10}R^{11}$ in which $R^9$, $R^{10}$ and $R^{11}$, independently of one another, are hydrogen or $C_1-C_4$-alkyl, which process comprises reacting an anthraquinone compound of the formula (1B)

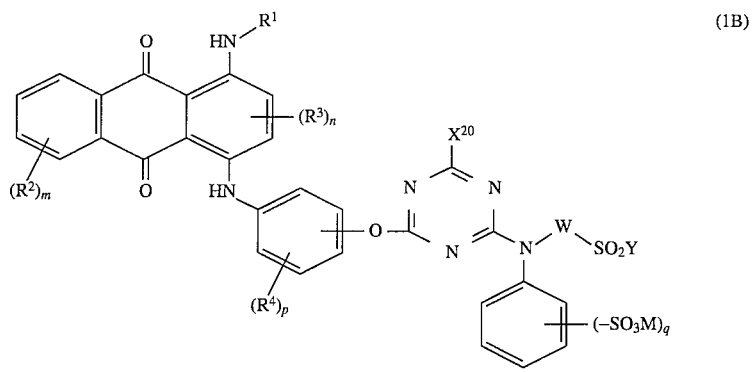

in which $X^{20}$ is chlorine or fluorine, with ammonia, $H_2NCN$, a carboxy-$(C_1-C_4)$-alkylamine, $C_1-C_4$-alkylamine, di-$(C_1-C_4$-alkyl)aznine, $C_6$-arylamine where the alkyl and aryl radicals of the alkylamino and arylamino groups mentioned are unsubstituted or contain 1 to 5 substituents selected from the group consisting of hydroxyl, $C_1$–$C_4$-alkoxy, carboxyl, sulfo, sulfato, $C_1$–$C_4$-alkylsulfonyl, $C_6$-arylsulfonyl, halogen, cyano and nitro, or with a heterocyclic or aliphatic amine, which may contain 1 to 2 further hetero atoms selected from the group consisting of N, O and S and can be substituted by a carboxyl radical or an aminocarbonyl radical, or with a mono-, di- or tri-($C_1$–$C_4$-alkyl)ammonium salt.

13. A method for dyeing or printing a hydroxyl-, mercapto-, amino- or carboxamido-containing material or a material containing a combination of these groups comprising the step of dyeing or printing said material with an anthraquinone compound of the formula (1) as claimed in claim 1.

14. The method as claimed in claim 13, wherein the dyeing is a textile printing method or a short-liquor pad-dyeing method.

15. A method for discharge printing a hydroxyl-, mercapto-, amino- or carboxamido-containing material or a material containing a combination of these groups comprising the step of discharge printing said material with an anthraquinone compound as claimed in claim 9.

* * * * *